United States Patent
Weickgenannt et al.

(10) Patent No.: US 9,873,658 B2
(45) Date of Patent: Jan. 23, 2018

(54) PROCESS FOR HYDROGENATING 4,4'-METHYLENEDIANILINE

(71) Applicant: BASF SE, Ludwigshafen (DE)

(72) Inventors: Andreas Weickgenannt, Mannheim (DE); Bernd Bastian Schaack, Bensheim (DE); Barbara Wucher, Laudenbach (DE); Alexander Panchenko, Ludwigshafen (DE); Frank Hettche, Weinheim (DE); Martin Bock, Ludwigshafen (DE); Aik Meam Tan, Speyer (DE); Kirsten Dahmen, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/103,789

(22) PCT Filed: Dec. 10, 2014

(86) PCT No.: PCT/EP2014/077120
§ 371 (c)(1),
(2) Date: Jun. 10, 2016

(87) PCT Pub. No.: WO2015/086638
PCT Pub. Date: Jun. 18, 2015

(65) Prior Publication Data
US 2016/0326094 A1    Nov. 10, 2016

(30) Foreign Application Priority Data

Dec. 11, 2013 (EP) ..................... 13196584

(51) Int. Cl.
| | |
|---|---|
| *C07C 209/72* | (2006.01) |
| *B01J 23/46* | (2006.01) |
| *B01J 35/10* | (2006.01) |
| *B01J 37/02* | (2006.01) |
| *B01J 37/08* | (2006.01) |
| *B01J 37/18* | (2006.01) |

(52) U.S. Cl.
CPC .......... *C07C 209/72* (2013.01); *B01J 23/462* (2013.01); *B01J 35/1014* (2013.01); *B01J 35/1038* (2013.01); *B01J 35/1042* (2013.01); *B01J 37/0225* (2013.01); *B01J 37/0236* (2013.01); *B01J 37/08* (2013.01); *B01J 37/18* (2013.01); *Y02P 20/582* (2015.11)

(58) Field of Classification Search
None
See application file for complete search history.

(56) References Cited

U.S. PATENT DOCUMENTS

| | | |
|---|---|---|
| 2002/0087036 A1 | 7/2002 | Haas et al. |
| 2010/0292510 A1 | 11/2010 | Pfeffinger et al. |
| 2011/0137083 A1 | 6/2011 | Pfeffinger |

FOREIGN PATENT DOCUMENTS

| | | |
|---|---|---|
| DE | 195 33 718 A1 | 3/1997 |
| EP | 0 111 238 B1 | 1/1986 |
| EP | 1 106 600 A2 | 6/2001 |
| EP | 1 337 331 B1 | 1/2007 |
| EP | 1 366 812 B1 | 2/2009 |
| WO | 2008/015135 A2 | 2/2008 |
| WO | 2008/083997 A1 | 7/2008 |
| WO | 2009/090179 A2 | 7/2009 |
| WO | 2009/153123 A1 | 12/2009 |
| WO | 2011/003899 A1 | 1/2011 |

OTHER PUBLICATIONS

Materials Design, "Temperature-Dependent Phase Transitions of ZrO2", 2009, 1-4.*
International Search Report dated Feb. 10, 2015, in PCT/EP2014/077120 Filed Dec. 10, 2014.

* cited by examiner

*Primary Examiner* — Clinton Brooks
(74) *Attorney, Agent, or Firm* — Oblon, McClelland, Maier & Neustadt, L.L.P.

(57) ABSTRACT

The present invention relates to a process for hydrogenating 4,4'-methylenedianiline and/or polymeric MDA with hydrogen in the presence of a catalyst comprising ruthenium on a zirconium oxide support material, and also to the use of a catalyst comprising ruthenium on a zirconium oxide support material for hydrogenating 4,4'-methylenedianiline and/or polymeric MDA.

20 Claims, No Drawings

PROCESS FOR HYDROGENATING 4,4'-METHYLENEDIANILINE

The present invention relates to a process for hydrogenating 4,4'-methylenedianiline (MDA) and/or polymeric MDA with hydrogen in the presence of a catalyst comprising ruthenium on a zirconium oxide support material, and also to the use of a catalyst comprising ruthenium on a zirconium oxide support material for hydrogenating 4,4'-methylenedianiline (MDA) and/or polymeric MDA.

Processes for hydrogenating organic compounds, in particular for hydrogenating aromatic compounds to form the corresponding cyclohexane derivatives, are already known from the prior art.

WO 2009/153123 A1 discloses a continuous process and a reactor for hydrogenating organic compounds in a multiphase system in the presence of a homogeneous or heterogeneous catalyst, the process being carried out in two stages. Possible catalysts disclosed according to this document include heterogeneous catalysts comprising, for example, noble metals such as platinum, palladium, ruthenium and rhodium or other transition metals, for example molybdenum, tungsten and chromium. These heterogeneous catalysts may be present on support materials. Appropriate support materials include, for example, carbon, aluminum oxide, silicon dioxide, zirconium dioxide, zeolites, aluminosilicates or mixtures of these support materials. In Example 1, an MDA melt was hydrogenated in the presence of a suspended Ru(IV) oxide hydrate catalyst. The application does not contain examples concerning the hydrogenation of MDA in the presence of Ru supported on zirconium oxide. Substrates preferably used in this process include aromatic compounds comprising amino substitutents, for example MDA, polymeric MDA, aniline, 2,4-diaminotoluene, 2,6-diaminotoluene, o-phenylenediamine etc. The heterogeneous catalysts are used in suspension.

DE 19533718 A1 discloses a process for hydrogenating aromatic compounds having at least one amino group bonded to an aromatic core. A heterogeneous catalyst comprising ruthenium and optionally at least one metal of transition group I, VII or VIII may be used therefor. Support materials used include, for example, aluminum oxide, silicon dioxide, titanium dioxide or zirconium dioxide, preferably aluminum dioxide or zirconium dioxide. Only one example is given of a catalyst comprising ruthenium on the support material aluminum oxide, but not zirconium oxide.

EP 1337331 B1 discloses a process for catalytically hydrogenating aromatic or heteroaromatic amines, wherein the active metal is ruthenium and the catalyst comprises at least one further metal of transition group I, VII, or VIII and these have been applied to a support material having a BET($N_2$) surface area of less than 10 $m^2/g$. Aromatic compounds used include, for example, 4,4'-MDA and isomers thereof.

EP 0111238 B1 discloses a process for catalytically hydrogenating 4,4'-MDA, wherein the hydrogenation is carried out in the presence of both ruthenium on a support material and 65 to 700 wt %, based on the amount of ruthenium, of a moderator selected from the group consisting of the nitrates and sulfates of the alkali metals and the nitrates of the alkaline earth metals. Such an additive is not knowingly added to the process according to the invention.

EP 1366812 B1 discloses a process for hydrogenating an aromatic amine in the presence of the active metal ruthenium on a support material. The BET surface area of the support material used in the process is in the range from greater than 30 $m^2/g$ to less than 70 $m^2/g$. Support materials disclosed include, inter alia, aluminum oxide, silicon oxide, titanium oxide and zirconium oxide. In the examples, only aluminum oxide is used as support material, but not zirconium oxide.

WO 2011/003899 A1 discloses a process for hydrogenating organic compounds, for example aromatic compounds. To this end, a heterogeneous catalyst may be used which comprises noble metals, for example platinum, palladium, ruthenium, osmium, iridium and rhodium or other transition metals. Support materials mentioned include, for example, aluminum oxide, silicon dioxide, titanium dioxide and activated carbon, but not zirconium oxide.

WO2009/090179 A2 discloses a process for preparing cycloaliphatic amines by hydrogenating the corresponding aromatic compounds. This is achieved using a ruthenium-containing catalyst in the form of a suspension, suspended inorganic additives being added to said catalyst. These additives comprise, inter alia, zirconium oxide. In this case the additive does not serve as support material since the ruthenium is not applied thereto prior to use in the hydrogenation.

In the hydrogenation, i.e., in the ring hydrogenation, of 4,4'-methylenedianiline to form 4,4'-diaminocyclohexylmethane, three isomers may be formed, namely trans,trans-4,4'-diaminocyclohexylmethane, cis,trans-4,4'-diaminocyclohexylmethane and cis,cis-4,4'-diaminocyclohexylmethane. These isomers, more particularly their proportions in the mixture obtained, have a distinct influence on the physical properties, for example the melting point, of the mixture. In order to obtain a very low melting point, it is, for example, advantageous for the proportion of the trans,trans product in the product mixture obtained to be very low.

Polymeric MDA is known per se to those skilled in the art. In particular, those skilled in the art understand the term to mean oligomeric or polymeric addition products of 4,4'-methylenedianiline, for example comprising 2 to 100, more particularly 3 to 7, repeating units of 4,4'-methylenedianiline. In the hydrogenation according to the invention, the polymeric MDA used is converted to the corresponding ring-hydrogenated oligomers or polymers. For every individual 4,4'-methylenedianiline unit, the corresponding trans, trans, cis,trans, or cis,cis isomers may be obtained. It is preferable to use the process according to the invention to obtain a corresponding oligomeric or polymeric ring-hydrogenated compound having a very low proportion of trans, trans repeating units.

It is accordingly an object of the present invention to provide a process for hydrogenating 4,4'-methylenedianiline to form 4,4'-diaminocyclohexylmethane and/or for hydrogenating polymeric MDA to form the corresponding ring-hydrogenated compound, using a catalyst which has a particularly high activity over a long period of time and therefore achieves a high conversion over a long period of time and which further provides a product mixture, i.e., a mixture of the three isomers trans,trans-4,4'-diaminocyclohexylmethane, cis,trans-4,4'-diaminocyclohexylmethane and cis,cis-4,4'-diaminocyclohexylmethane and/or corresponding oligomeric or polymeric ring-hydrogenated compounds, which features a particularly low proportion of the trans,trans isomer and, as a result, a low melting point. Furthermore, the process according to the invention may be carried out in a fixed bed or in suspension without the disadvantages known from the prior art occurring, for example coking or sintering of the catalyst in a fixed-bed reaction.

These objects are achieved by the process according to the invention for hydrogenating 4,4'-methylenedianiline and/or polymeric MDA with hydrogen in the presence of a catalyst comprising ruthenium on a zirconium oxide support material. The objects are further achieved by the use of a catalyst comprising ruthenium on a zirconium oxide support material for hydrogenating 4,4'-methylenedianiline and/or polymeric MDA.

The present invention is notable in that a catalyst comprising ruthenium on a zirconium oxide support material is used in order to hydrogenate 4,4'-methylenedianiline to form 4,4'-diaminocyclohexylmethane and/or to hydrogenate polymeric MDA to form the corresponding ring-hydrogenated compound, the trans,trans isomer of the desired compound being present in a small proportion.

The compound 4,4'-methylenedianiline (MDA) (I), known to those skilled in the art, is used in the process according to the invention.

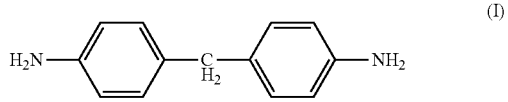 [SMILES: Nc1ccc(Cc2ccc(N)cc2)cc1]

(I)

This compound is commercially available or may be prepared according to the process known to those skilled in the art and described, for example, in WO 2008/083997.

In accordance with the invention, pure 4,4'-methylenedianiline may be used. It is also possible, in accordance with the invention, to use 4,4'-methylenedianiline which, in addition to the desired isomer, comprises 2,4'-methylenedianiline (II) and, as the case may be, further isomers in a proportion of up to 30 wt %, preferably up to 7 wt %, in each case based on the total amount of methylenedianiline used.

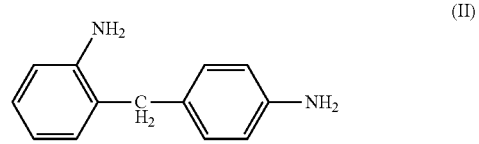 [SMILES: Nc1ccc(Cc2ccccc2N)cc1]

(II)

4,4'-Methylenedianiline is ring-hydrogenated by the process according to the invention, i.e., the corresponding isomeric dicyclohexyl derivatives are obtained. The individual isomers of 4,4'-diaminocyclohexylmethane. i.e., trans,trans-4,4'-diaminocyclohexylmethane (IIIa), cis,trans-4,4'-diaminocyclohexylmethane (IIIb) and cis,cis-4,4'-diaminocyclohexylmethane (IIIc), are depicted below.

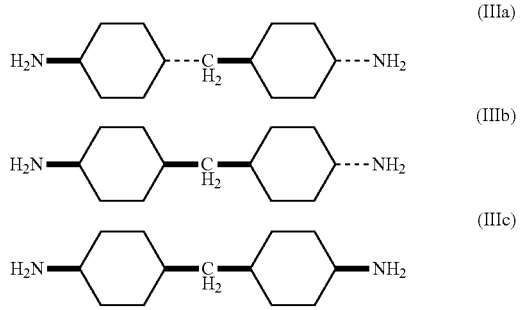

(IIIa)

(IIIb)

(IIIc)

The process according to the invention preferably gives a product which, without further purification of the reactor discharge, comprises the trans,trans isomer in an amount of less than 25 wt %, preferably less than 23 wt %, in each case based on the total amount of product obtained, the remaining proportion being accounted for by the cis,trans and/or cis,cis isomers and, as the case may be, by hydrogenation products of 2,4'-methylenedianiline.

In a preferred embodiment of the process according to the invention, the product obtained is a mixture comprising the isomers of 4,4'-diaminodicyclohexylmethane, said mixture comprising the trans,trans isomer in an amount of from 10 to 30 wt %, preferably 10 to 26 wt %, the cis,trans isomer in an amount of from 30 to 55 wt %, preferably 40 to 55 wt %, and the cis,cis isomer in an amount of from 10 to 50 wt %, preferably 25 to 40 wt %, in each case based on the total amount of all isomers present, the sum of the isomers present always totaling 100 wt %.

In a further preferred embodiment of the process according to the invention, starting from polymeric MDA, the product obtained is a mixture of corresponding oligomeric or polymeric ring-hydrogenated compounds comprising as repeating units the isomers of 4,4'-diaminodicyclohexylmethane, said mixture comprising as repeating units the trans,trans isomer in an amount of from 10 to 30 wt %, preferably 10 to 26 wt %, the cis,trans isomer in an amount of from 30 to 55 wt %, preferably 40 to 55 wt %, and the cis,cis isomer in an amount of from 10 to 50 wt %, preferably 25 to 40 wt %, in each case based on the total amount of all isomeric repeating units present, the sum of all isomers present always totaling 100 wt %.

The proportions of the individual isomers comprised in the product obtained according to the invention can be determined by analytical methods known to those skilled in the art. A preferred analytical method is gas chromatography (GC), which is known to those skilled in the art.

A product preferably obtained according to the invention, having the abovementioned low proportions of trans,trans isomer, has a melting point below 40° C., preferably below 30° C., and more preferably below 22° C. A preferred lower limit for the melting point is, for example, 0° C. The process according to the invention can generally be carried out as a continuous operation or batchwise. In a preferred embodiment, the present invention relates to the process according to the invention carried out as a continuous operation.

The process according to the invention can generally be carried out in suspension or in a fixed bed.

The present invention therefore preferably relates to the process according to the invention carried out in suspension or in a fixed bed.

When the reaction is carried out batchwise, the hydrogenation can be carried out, for example, in a stirred tank or a stirred autoclave, in a loop reactor, a jet loop reactor, a bubble column or in a fixed-bed reactor with a pumped circulation circuit. It is preferred that the batchwise hydrogenation is carried out in a stirred tank or a stirred autoclave.

When the reaction is carried out as a continuous operation, the hydrogenation is usually carried out in a continuously operated stirred tank reactor, a continuously operated loop reactor, a continuously operated jet loop reactor, a continuously operated bubble column or a continuously operated fixed-bed reactor with a pumped circulation circuit, or in a stirred tank cascade.

It is preferable to carry out the process in trickle reactors or in flooded mode by the fixed-bed mode, for example according to WO 2008/015135 A1. The hydrogen may be passed over the catalyst either in cocurrent with the solution of the reactant to be hydrogenated or in countercurrent.

Useful apparatuses for carrying out a hydrogenation over a fluidized catalyst bed and over a fixed catalyst bed are known from the prior art, for example from Ullmanns Enzyklopädie der Technischen Chemie, 4th edition, volume 13, p. 135 ff., and also from P. N. Rylander, "Hydrogenation and Dehydrogenation" in Ullmann's Encyclopedia of Industrial Chemistry, 5th ed. on CD-ROM.

In order to attain complete conversion, the hydrogenation discharge may be post-reacted. To this end, the hydrogenation discharge may, following the hydrogenation process, be passed through one or more downstream reactors in the gas phase or in the liquid phase in straight pass or by pumping in circulation. If liquid phase hydrogenation is concerned, the reactor can be operated in trickle mode or in flooded mode. The reactor is packed with the catalyst according to the invention or with another catalyst known to those skilled in the art.

Useful reactors for carrying out the process according to the invention in suspension mode are known per se to those skilled in the art, for example stirred tanks or bubble columns. In accordance with the invention, a cascade of two or more serially connected suspension reactors may also be used, for example a stirred tank cascade or a bubble column cascade, for example each having at least three equivalent serially connected reactors.

The process according to the invention is generally carried out at a pressure of from 50 to 500 bar, preferably at a pressure of from 60 to 300 bar.

The present invention therefore preferably relates to the process according to the invention carried out at a pressure of from 60 to 300 bar.

Since it is particularly preferable for the process according to the invention to be carried out without the addition of a further gas in addition to hydrogen, the process pressure is preferably determined by the partial hydrogen pressure. It is therefore particularly preferable for the present invention to relate to the process according to the invention carried out at a hydrogen pressure of from 50 to 500 bar, preferably 60 to 300 bar.

According to the invention, the process is generally carried out at a temperature of from 30 to 280° C., preferably at a temperature of from 60 to 250° C.

In the preferred embodiment that the process according to the present invention is carried out in a fixed bed, it is preferably carried out at a temperature of from 50 to 190° C., preferably 70 to 120° C.

The present invention therefore preferably relates to the process according to the invention carried out in a fixed bed at a temperature of from 50 to 190° C., preferably 70 to 120° C.

In the further preferred embodiment that the process according to the present invention is carried out in suspension, it is preferably carried out at a temperature of from 50 to 190° C., preferably 100 to 140° C.

The present invention therefore preferably relates to the process according to the invention carried out in suspension at a temperature of from 50 to 190° C., preferably 100 to 140° C.

In the process according to the invention, hydrogen is used as hydrogenating agent.

In a preferred embodiment, the hydrogen used as the hydrogenating agent is used in an excess based on the compound to be hydrogenated. For example, hydrogen is used as hydrogenating agent in a 1.01- to 10-fold, preferably 1.05- to 10-fold, more preferably 1- to 10-fold, and most preferably 1.01- to 5-fold stoichiometric excess, for example in a 1.1- to 5-fold stoichiometric excess. In one embodiment, the hydrogen employed can be recycled into the reaction as cycle gas.

In a preferred embodiment of the process according to the invention, hydrogen of technical-grade purity is used. In the context of the present invention, "technical-grade purity" is to be understood as denoting a hydrogen content of at least 99.0 wt %, preferably at least 99.5 wt %.

In a further embodiment according to the invention, the hydrogen can also be used in the form of a gas comprising hydrogen. By way of example, mixtures comprising gases and inert gases such as nitrogen, helium, neon, argon, ammonia and/or carbon dioxide may be used. Gases comprising hydrogen may include, for example, reformer off-gases, refinery gases, etc. These gases comprising hydrogen have a hydrogen content of, for example, 10 to 100 wt %, preferably 50 to 100 wt %.

The process according to the invention can generally be carried out in the presence or absence of at least one solvent. It is particularly preferable to carry out the process in an organic solvent. In a further preferred embodiment, the process according to the invention is carried out in the absence of a solvent, i.e., as a melt.

The use of solvents is, for example, advantageous when the organic compound is present as a solid and cannot or can only with great difficulty be handled and conveyed as a melt. Suitable solvents include, for example, those selected from the group consisting of alcohols, for example isopropanol, isobutanol or t-butanol, ethers, for example diethyl ether, diethylene glycol dimethyl ether (diglyme), dipropylene glycol dimethyl ether (proglyme), dioxane or tetrahydrofuran, and mixtures thereof. In a preferred embodiment, dioxane or proglyme is used as solvent. In a further embodiment according to the invention, methyldiaminocyclohexane is used. In a further embodiment according to the invention, the product formed in the reaction, i.e., 4,4'-diaminocyclohexylmethane, in particular a mixture of isomers according to the invention, comprising trans,trans-4,4'-diaminocyclohexylmethane, cis,trans-4,4'-diaminocyclohexylmethane and cis,cis-4,4'-diaminocyclohexylmethane, or the low boilers formed, for example 4-aminocyclo-hexylmethylcyclohexane, is used as solvent.

When the process according to the invention is carried out in the presence of a solvent, the solvent is generally used in an amount such that a 2 to 50 wt %, preferably a 5 to 40 wt %, and more preferably an 8 to 30 wt % solution of the product to be hydrogenated is present.

According to the invention, the catalyst used is ruthenium on a zirconium oxide support material.

Appropriate catalysts may be prepared by known processes such as impregnation, described, for example, in A. B. Stiles, Catalyst Manufacture—Laboratory and Commercial Preparations, Marcel Dekker, New York, 1983, or precipitation, described, for example, in EP 1 106 600, page 4, and A. B. Stiles, Catalyst Manufacture, Marcel Dekker, Inc., 1983, page 15.

The catalysts to be used according to the invention can be prepared by applying useful ruthenium compounds, for example ruthenium salts, to extrudates, pellets or spheres of the zirconium oxide support material having diameters, for example, from about 1.5 to 10 mm. Subsequently, the catalyst is generally dried at a temperature of from 80 to 180° C., for example 120° C., and calcined at a temperature of from 180 to 450° C., for example 180° C.; both steps may also be effected simultaneously. Ruthenium salts useful for application include, for example, those selected from the group consisting of ruthenium acetate, acetylacetonate, chloride, nitrosyl nitrate and mixtures thereof.

An accordingly prepared catalyst is generally ready for use according to the invention following the drying step. It is, however, preferable to activate the catalyst by treatment with hydrogen at a temperature of, for example, 150 to 400° C. before use, and it is more preferable to do so after the catalyst has been placed in the reactor provided for the hydrogenation according to the invention.

Ruthenium is preferably present on the catalyst used in accordance with the invention in a total amount of from 0.05 to 15 wt % or more than 15 to 20 wt %, i.e., 0.05 to 20 wt %, preferably 0.05 to 12 wt % or more than 12 to 15 wt %, i.e., 0.05 to 15 wt %, more preferably 0.1 to 11 wt % or more than 11 to 15 wt %, i.e., 0.01 to 15 wt %, in each case based on the total weight of the catalyst.

It is preferable according to the invention for the support material zirconium oxide ($ZrO_2$) to be present in monoclinic, tetragonal, cubic or amorphous phase, or in a mixed phase, monoclinic or tetragonal phase or a mixed phase of these forms being particularly preferable.

It is therefore preferable for the present invention to relate to the process according to the invention, wherein the zirconium oxide support material is present in monoclinic, tetragonal, cubic or amorphous phase, or in a mixed phase of these modifications.

The present invention further preferably relates to the process according to the invention, wherein the zirconium oxide support material is present in monoclinic, tetragonal, cubic or amorphous phase, or in a mixed phase of these modifications.

It is preferable according to the invention, for the zirconium oxide support material, preferably prior to applying ruthenium, to have a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption according to DIN 66131.

It is preferable according to the invention, for the zirconium oxide support material, preferably prior to applying ruthenium, to have a pore volume of from 0.1 to 1 $cm^3/g$, preferably 0.1 to 0.9 $cm^3/g$, in each case determined by mercury porosimetry according to DIN 66133.

It is preferable according to the invention, for the zirconium oxide support material of the inventive catalyst used in suspension, preferably prior to applying ruthenium, to have a pore volume of from 0.1 to 1 $cm^3/g$, preferably 0.5 to 1 $cm^3/g$, more preferably 0.7 to 0.9 $cm^3/g$, in each case determined by mercury porosimetry according to DIN 66133.

It is preferable according to the invention, for the zirconium oxide support material of the invention catalyst used in a fixed bed, preferably prior to applying ruthenium, to have a pore volume of from 0.1 to 1 $cm^3/g$, preferably 0.1 to 0.6 $cm^3/g$, more preferably 0.1 to 0.5 $cm^3/g$, in each case determined by mercury porosimetry according to DIN 66133.

It is preferable according to the invention, for the zirconium oxide support material, preferably prior to applying the ruthenium, to have a tamped density of from 500 to 2000 $kg/m^3$, preferably 600 to 1800 $kg/m^3$, more preferably 700 to 1750 $kg/m^3$, in each case determined in a STAV2003 tamping volumeter from JEL, the sample having been tamped 2000 times.

It is particularly preferable according to the invention, for the zirconium oxide support material, preferably prior to applying the ruthenium, to have a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption, a pore volume of from 0.1 to 1 $cm^3/g$, preferably 0.1 to 0.8 $cm^3/g$, more preferably 0.1 to 0.7 $cm^3/g$, in each case determined by mercury porosimetry, and a tamped density of from 500 to 2000 $kg/m^3$, preferably 600 to 1750 $kg/m^3$, more preferably 700 to 1500 $kg/m^3$, in each case determined in a STAV2003 tamping volumeter from JEL, the sample having been tamped 2000 times.

The present invention therefore preferably relates to the process according to the invention, wherein the zirconium oxide support material, preferably prior to applying the ruthenium, has a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption, a pore volume of from 0.1 to 1 $cm^3/g$, preferably 0.1 to 0.8 $cm^3/g$, more preferably 0.1 to 0.7 $cm^3/g$, in each case determined by mercury porosimetry, and a tamped density of from 500 to 2000 $kg/m^3$, preferably 600 to 1800 $kg/m^3$, more preferably 700 to 1500 $kg/m^3$, in each case determined in a STAV2003 tamping volumeter from JEL, the sample having been tamped 2000 times.

It is particularly preferable according to the invention for the zirconium oxide support material, preferably prior to applying the ruthenium, to have a monoclinic or tetragonal modification (or a mixture of both of these), a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption, a pore volume of from 0.1 to 1 $cm^3/g$, preferably 0.1 to 0.8 $cm^3/g$, more preferably 0.1 to 0.7 $cm^3/g$, in each case determined by mercury porosimetry, and a tamped density of from 500 to 2000 $kg/m^3$, preferably 600 to 1800 $kg/m^3$, more preferably 700 to 1500 $kg/m^3$, in each case determined in a STAV2003 tamping volumeter from JEL, the sample having been tamped 2000 times.

The present invention therefore preferably relates to the process according to the invention, wherein the zirconium oxide support material, preferably prior to applying the ruthenium, has a monoclinic or tetragonal modification (or a mixture of both of these), a BET surface area of from 30 to 300 $m^2/g$, preferably 35 to 250 $m^2/g$, more preferably 50 to 90 $m^2/g$ or more than 90 to 100 $m^2/g$, i.e., 50 to 100 $m^2/g$, in each case determined by nitrogen sorption, a pore volume of from 0.1 to 1 $cm^3/g$, preferably 0.1 to 0.8 $cm^3/g$, more preferably 0.1 to 0.7 $cm^3/g$, in each case determined by mercury porosimetry, and a tamped density of from 500 to 2000 $kg/m^3$, preferably 600 to 1800 $kg/m^3$, more preferably 700 to 1500 $kg/m^3$, in each case determined in a STAV2003 tamping volumeter from JEL, the sample having been tamped 2000 times. It is preferable according to the invention for the zirconium oxide support material of the catalyst used in the fixed bed to have a pore size distribution where more than 50% of the pores present are formed by mesopores having a diameter of from 2 nm to 50 nm and the remainder to 100% are formed by macropores having a diameter of >50 nm.

The present invention therefore preferably relates to the process according to the invention, wherein the zirconium oxide support material of the catalyst used in the fixed bed has a pore size distribution where more than 50% of the pores present are formed by mesopores having a diameter of from 2 nm to 50 nm and the remainder to 100% are formed by macropores having a diameter of >50 nm.

It is preferable according to the invention for the zirconium oxide support material of the catalyst used in suspension to have a pore size distribution where more than 40% of the pores present are macropores having a diameter of >50 nm and the remainder to 100% are formed by mesopores having a diameter of from 2 nm to 50 nm.

The present invention therefore preferably relates to the process according to the invention, wherein the zirconium oxide support material of the catalyst used in suspension has a pore size distribution where more than 40% of the pores present are macropores having a diameter of >50 nm and the remainder to 100% are formed by mesopores having a diameter of from 2 nm to 50 nm.

The present invention preferably relates to the process according to the invention, wherein the catalyst has a BET surface area of from 30 to 300 m$^2$/g, preferably 50 to 90 m$^2$/g or more than 90 to 100 m$^2$/g, i.e., 50 to 100 m$^2$/g, a pore volume of from 0.1 to 1 cm$^3$/g, preferably 0.1 to 0.9 cm$^3$/g, and a tamped density of from 500 to 2000 kg/m$^3$, preferably 700 to 1750 kg/m$^3$.

The present invention preferably also relates to the process according to the invention, wherein the catalyst used in the fixed bed has a pore size distribution where more than 50% of the pores present are formed by mesopores having a diameter of from 2 nm to 50 nm and the remainder to 100% are formed by macropores having a diameter of >50 nm.

The present invention preferably also relates to the process according to the invention, wherein the catalyst used in suspension has a pore size distribution where more than 40% of the pores present are formed by macropores having a diameter of >50 nm and the remainder to 100% are formed by mesopores having a diameter of from 2 nm to 50 nm.

It is particularly preferable for the catalytically active metal ruthenium comprised in the catalyst used according to the invention to be distributed over all of the support material, i.e., distributed over the entire diameter of a support material particle, i.e., according to the invention, the catalytically active ruthenium is essentially homogeneously distributed over all of the support material, i.e., over the entire diameter of a support material particle.

In the process according to the invention, a space velocity over the catalyst of from 0.01 to 2 kg, preferably 0.01 to 1 kg, more preferably 0.02 to 0.6 kg and most preferably 0.02 to 0.2 kg of organic compound to be hydrogenated per liter of catalyst per hour is generally established. Any small change in the proportion of the desired product attained during the process according to the invention due to any change in catalyst activity over the course of particularly long reaction periods can be compensated by a small adjustment to the reaction temperature or to the other parameters. The potentially varying proportions of desired product can be monitored by analysis of the reaction mixture. This analysis can be carried out using methods known to those skilled in the art, for example gas chromatography (GC).

The process according to the invention can generally be carried out until a useful conversion is attained. When the process according to the invention is carried out continuously, the reaction time corresponds to the residence time of the reaction mixture in the continuously operated reactor. It is preferable according to the invention for the reaction time to be 10 to 400 min.

The present invention therefore preferably relates to the process according to the invention, wherein the reaction time is 10 to 400 min.

The hydrogenation mixtures obtained according to the invention can be purified after the process according to the invention, for example by distillation. Any catalyst present in the reaction output can be removed prior to the distillation, for example by a solid-liquid separation, for example filtration, sedimentation or centrifugation. Solvent and unconverted starting materials can be recycled into the process.

After successful work-up, for example by distillation, the desired products according to the invention are obtained in a purity of at least 99 wt %. In this purity, the abovementioned compounds are generally usable for all further processes.

Using the process according to the invention, it is possible to obtain the desired product having a small proportion of the trans,trans isomer. It is possible in accordance with the invention that the desired isomer distribution is achieved by the hydrogenation alone and that the isomer distribution need not be altered in an optional distillative work-up for removal of solvent, unconverted reactant and any by-products formed.

The present invention also relates to the use of a catalyst comprising ruthenium on a zirconium oxide support material for hydrogenating 4,4'-methylenedianiline (MDA) to form a mixture comprising the isomers of 4,4'-diaminodicyclohexylmethane, wherein said mixture comprises the trans,trans isomer in an amount of from 10 to 30 wt %, preferably 10 to 26 wt %, the cis,trans isomer in an amount of from 30 to 55 wt %, preferably 40 to 55 wt %, and the cis,cis isomer in an amount of from 10 to 50 wt %, preferably 25 to 40 wt %, in each case based on the total amount of all isomers present, wherein the sum of the isomers present in each case totals 100 wt %, and/or for hydrogenating polymeric MDA, wherein oligomeric or polymeric ring-hydrogenated compounds comprising the isomers of 4,4'-diaminodicyclohexylmethane as repeating units are obtained as product, wherein said product comprises the trans,trans isomer in an amount of from 10 to 30 wt %, preferably 10 to 26 wt %, the cis,trans isomer in an amount of from 30 to 55 wt %, preferably 40 to 55 wt %, and the cis,cis isomer in an amount of from 10 to 50 wt %, preferably 25 to 40 wt %, in each case based on the total amount of all isomers present, wherein the sum of all isomers present in each case totals 100 wt %.

The present invention further relates to the use of a catalyst comprising ruthenium on a zirconium oxide support material for hydrogenating 4,4'-methylenedianiline (MDA) to form a mixture comprising the isomers of 4,4'-diaminodicyclohexylmethane and/or for hydrogenating polymeric MDA to form corresponding oligomeric or polymeric ring-hydrogenated compounds having a melting point of less than 40° C., preferably less than 30° C., more preferably less than 22° C. A preferred lower limit for the melting point is 0° C.

The cycloaliphatic amines obtainable by the process according to the invention can be used as synthetic building blocks for the preparation of surfactants, medicaments and crop protection agents, stabilizers including light stabilizers, polymers, polyamides, isocyanates, hardeners for epoxy resins, catalysts for polyurethanes, intermediates for preparing quaternary ammonium compounds, plasticizers, corrosion inhibitors, synthetic resins, ion exchangers, textile auxiliaries, dyes, vulcanization accelerants, emulsifiers and/or as starting substances for the preparation of ureas and polyureas.

In particular, the hydrogenation products of bis(4-aminophenyl)methane (MDA) can be used as monomer building blocks for polyamides.

Therefore, the present invention also further relates to the use of a mixture comprising the isomers of 4,4'-diaminodicyclohexylmethane, wherein said mixture comprises the trans,trans isomer in an amount of from 10 to 30 wt %, preferably 10 to 26 wt %, the cis,trans isomer in an amount of from 30 to 55 wt %, preferably 40 to 55 wt %, and the cis,cis isomer in an amount of from 10 to 50 wt %, preferably 25 to 40 wt %, in each case based on the total amount of all isomers present, wherein the sum of all isomers present always totals 100 wt %, as synthetic building blocks for the preparation of surfactants, medicaments and crop protection agents, stabilizers including light stabilizers, polymers, polyamides, isocyanates, hardeners for epoxy resins, catalysts for polyurethanes, intermediates for preparing quaternary ammonium compounds, plasticizers, corrosion inhibitors, synthetic resins, ion exchangers, textile auxiliaries, dyes, vulcanization accelerators, emulsifiers and/or as starting substances for the preparation of ureas and polyureas.

As regards the individual features and the preferred embodiments of this use according to the invention, what has been said in respect of the process of the invention applies correspondingly to the use according to the invention.

The process according to the invention and its advantages are described in more detail using the following examples.

EXAMPLES

Preparation of the Catalysts According to the Invention

1. Preparation of Fixed-Bed Catalyst 1% Ru on $ZrO_2$ 238 g of $ZrO_2$ extrudates (diameter 3 mm, SZ 31108 from NorPro, BET surface area: 73 $m^2/g$, pore volume 0.30 ml/g, pore size distribution: 6% macropores, 94% mesopores) are sprayed with 19.81 g of Ru(III) nitrosyl nitrate (15.95 wt % Ru(III) nitrosyl nitrate (from Heraeus) in dilute nitric acid) diluted with 35 ml DM water, in an impregnation drum. The extrudates are then dried in a circulating air drying cabinet at 120° C. for 16 h and subsequently calcined in a muffle furnace at 180° C. for 2 h. The catalyst is then first reduced at 200° C. for 2 h (4 l/h $H_2$; 40 l/h $N_2$) and passivated at room temperature for 1 h with a mixture of 10 vol % air and 90 vol % $N_2$. The active material thus prepared contains 1 wt % Ru and 99 wt % zirconium oxide.

The catalyst thus prepared has the following characteristics: a BET surface area of 81 $m^2/g$, a tamped density of 1.2 kg/l, a pore volume of 0.24 ml/g (determined by Hg porosimetry).

2. Preparation of Suspension Catalyst 10% Ru on $ZrO_2$ 30.51 g of Ru(III) nitrosyl nitrate solution (15.95 wt % Ru(III) nitrosyl nitrate (from Heraeus) in dilute nitric acid) are added to a measuring cylinder and made up to a total volume of 37.5 ml with DM water. 50 g of zirconium oxide powder (D9-89, BASF, BET surface area: 78 $m^2/g$, pore volume: 0.84 ml/g, pore volume distribution: 68% macropores, 32% mesopores) are then added to a ceramic dish, the solution is added and mixed to homogeneity. The powder is subsequently dried in a circulating air drying cabinet at 120° C. for 16 h and calcined in air at 200° C. for 2 h. The powder is then first purged with 40 l/h of $N_2$ for 20 min in a rotary tube oven and then reduced over a period of 90 min (3 l/h hydrogen and 53 l/h nitrogen). Once the powder has cooled down to room temperature, the hydrogen is switched off and the powder is purged with about 60 l/h of nitrogen. In order to passivate the powder, 60 l/h of nitrogen and 1 l/h of air are initially introduced and the amount of air is then slowly raised to 10 l/h (0 l/h of nitrogen). Care must be taken to ensure the temperature of the catalyst does not exceed 35° C. The active material thus prepared contains 10 wt % Ru and 90 wt % $ZrO_2$. The catalyst thus prepared has the following characteristics: tamped density is 1.13 kg/l, the pore volume (Hg porosimetry) is 0.32 ml/g, the BET surface area 75 $m^2/g$; the pore distribution is as follows: 0% mesopores (2-50 mm), 100% macropores (>50 nm).

Example 1: Suspension Mode, Testing of Different Catalysts

A defined amount of the catalyst (150 mg) was added to a 10 ml autoclave along with 7 ml of a 9 wt % solution of 4,4'-methylenedianiline (MDA) in dioxane. The reaction mixture is subsequently heated to the appropriate reaction temperature under 140 bar of hydrogen pressure, with stirring, and held for 180 minutes. The solution is then cooled down to room temperature and the autoclave is decompressed to atmospheric pressure. The analysis of the reaction mixture is carried out by GC chromatography; the method is shown below. The results are shown in table 1.

The preparation of the catalysts was carried out analogously to the preparation of the catalyst according to the invention using appropriate metal salts/supports.

TABLE 1

| Metal | Metal content [%] | Support | Temp. [° C.] | Conversion [%] | Select. [%] | Isomer ratio [%] | | |
|---|---|---|---|---|---|---|---|---|
| | | | | | | trans/trans | cis/trans | cis/cis |
| Ru | 10 | $ZrO_2$ (mixture of monoclinic, tetragonal) | 120 | 91 | 85 | 16 | 49 | 35 |
| Pt | 1% | $ZrO_2$ (mixture of monoclinic, tetragonal) | 120 | 0 | 0 | | | |
| Ru | 9.4 | α-$Al_2O_3$ (CT19, Almatis) | 120 | 35 | 61 | 9 | 40 | 51 |
| Ru | 10 | Norit-SX Plus (Cabot Norit Activated Carbon) | 120 | 25 | 58 | 7 | 37 | 56 |
| Ru | 10 | $TiO_2$ (FINNTI S150, Kemira) | 120 | 98 | 55 | 12 | 44 | 44 |
| Ru | 9.4 | α-$Al_2O_3$ (CT19, Almatis) | 140 | 49 | 81 | 11 | 43 | 46 |
| Ru | 10 | Norit-SX Plus (Cabot Norit | 140 | 63 | 86 | 10 | 43 | 47 |

TABLE 1-continued

| Metal | Metal content [%] | Support | Temp. [° C.] | Conversion [%] | Select. [%] | Isomer ratio [%] | | |
|---|---|---|---|---|---|---|---|---|
| | | | | | | trans/trans | cis/trans | cis/cis |
| Ru oxihydrate | 75 | Activated Carbon) No support | 120 | 98 | 63 | 12 | 46 | 42 |

These examples show that the Ru/ZrO$_2$ catalyst according to the invention combines excellent reactivity with high selectivity.

Example 2: Suspension Mode, Testing of Different ZrO$_2$ Support Materials

A defined amount of the catalyst (10% Ru on ZrO$_2$, 150 mg) was added to a 10 ml autoclave along with 7 ml of a 9 wt % solution of 4,4'-methylenedianiline (MDA) in dioxane. The reaction mixture is subsequently heated to 120° C. under 140 bar of hydrogen pressure, with stirring, and held for 180 minutes. The solution is then cooled down to room temperature and the autoclave is decompressed to atmospheric pressure. The analysis of the reaction mixture is carried out by GC chromatography; the method is shown below. The results are shown in table 2. The preparation of the catalysts was carried out analogously to the preparation of the catalyst according to the invention using appropriate supports.

TABLE 2

| Support description | Pore volume [ml/g] | BET surface area [m$^2$/g] | Pore distribution (mesopores: macropores) | Conversion [%] | Selectivity [%] | Isomer ratio [%] | | |
|---|---|---|---|---|---|---|---|---|
| | | | | | | trans/trans | cis/trans | cis/cis |
| D9-89 | 0.84 | 75 | 32:68 | 91 | 85 | 16 | 49 | 35 |
| D9-89 (1000° C.) | 0.48 | 17 | 2:98 | 23 | 68 | 11 | 44 | 45 |

The Examples show that a low BET surface area results in a decline in selectivity and conversion and that a high BET surface area is advantageous.

Example 3: Suspension Mode, Optimization of the Reaction Conditions

A defined amount of the catalyst according to the invention (10 wt % Ru on ZrO$_2$) was added to a 10 ml autoclave along with 7 ml of a 9 wt % solution of 4,4'-methylenedianiline (MDA) in dioxane. The reaction mixture is subsequently heated to the appropriate reaction temperature under 140 bar of hydrogen pressure, with stirring, and held for a defined period of time. The solution is then cooled down to room temperature and the autoclave is decompressed to atmospheric pressure. The analysis of the reaction mixture is carried out by GC chromatography; the method is shown below. The results are shown in tables 3 and 4:

TABLE 3

| No. | T [° C.] | Reaction time [min] | Amount of catalyst [mg] | Conversion [%] | PACM selectivity [%] | Isomer ratio [%] | | |
|---|---|---|---|---|---|---|---|---|
| | | | | | | trans/trans | cis/trans | cis/cis |
| 1.1 | 100 | 120 | 75 | 67 | 14 | 10 | 44 | 46 |
| 1.2 | 100 | 300 | 37.5 | 56 | 9 | 9 | 42 | 49 |
| 1.3 | 120 | 240 | 150 | 100 | 49 | 29 | 50 | 21 |
| 1.4 | 120 | 240 | 75 | 100 | 95 | 19 | 49 | 32 |
| 1.5 | 120 | 240 | 37.5 | 100 | 91 | 14 | 47 | 39 |
| 1.6 | 140 | 240 | 150 | 100 | 48 | 57 | 36 | 7 |
| 1.7 | 140 | 240 | 75 | 100 | 93 | 49 | 41 | 10 |
| 1.8 | 140 | 240 | 37.5 | 100 | 94 | 38 | 47 | 15 |

PACM denotes 4,4'-diaminodicyclohexylmethane

The results of table 3 show that, with the aid of the catalyst according to the invention, the product PACM is obtained in an isomer ratio according to the invention at a reaction temperature of 120° C. Above 140° C., the isomer ratio changes so that the proportion of the trans,trans isomer increases significantly.

TABLE 4

| No. | T [° C.] | Reaction time [min] | Amount of catalyst [mg] | Conversion [%] | PACM selectivity [%] | Isomer ratio [%] | | |
|---|---|---|---|---|---|---|---|---|
| | | | | | | trans/trans | cis/trans | cis/cis |
| 1.9 | 120 | 120 | 75 | 99 | 85 | 14 | 46 | 40 |
| 1.10 | 120 | 180 | 75 | 91 | 85 | 16 | 49 | 35 |
| 1.11 | 120 | 240 | 75 | 100 | 95 | 19 | 49 | 32 |
| 1.12 | 140 | 120 | 75 | 100 | 93 | 35 | 48 | 17 |
| 1.13 | 140 | 180 | 75 | 100 | 94 | 45 | 44 | 11 |
| 1.14 | 140 | 240 | 75 | 100 | 93 | 49 | 41 | 10 |

PACM denotes 4,4'-diaminodicyclohexylmethane

The results of table 4 show that the proportion of trans,trans isomer in the product increases with increasing reaction time.

Example 4: Fixed-Bed Mode 120 ml of the passivated supported ruthenium catalyst according to the invention (1 wt % Ru on $ZrO_2$) were packed into a tubular reactor heated with an outer jacket (height: 1.4 m, interior diameter: 12 mm). Once initially flooded with hydrogen, the reactor was subsequently charged with a solution of 10 wt % of 4,4'-methylenedianiline (MDA). Hydrogenation was carried out at varying temperatures at a pressure of 140 bar, and the space velocity over the catalyst was 0.04 kg MDA/kg cat*h, the reactor being operated with circulation, i.e., part of the discharge is recycled into the reactor. The reaction discharges were analyzed by gas chromatography and the isomer distribution was determined. The method is shown below. The results are shown in table 5 and show that, using the catalyst according to the invention, a particularly low proportion of the trans,trans isomer, namely 19%, is attained at 80° C.

TABLE 5

| No. | T [° C.] | Conversion [%] | PACM selectivity [%] | Isomer ratio | | |
|---|---|---|---|---|---|---|
| | | | | trans/trans | cis/trans | cis/cis |
| 2.1 | 140 | 96 | 95 | 51 | 40 | 9 |
| 2.2 | 130 | 94 | 96 | 47 | 41 | 12 |

TABLE 5-continued

| No. | T [° C.] | Conversion [%] | PACM selectivity [%] | Isomer ratio | | |
|---|---|---|---|---|---|---|
| | | | | trans/trans | cis/trans | cis/cis |
| 2.3 | 100 | 84 | 86 | 28 | 49 | 23 |
| 2.4 | 80 | 67 | 60 | 19 | 49 | 32 |

PACM denotes 4,4'-diaminodicyclohexylmethane

Example 5: Fixed-Bed Mode

Further reactions according to the invention are carried out. The results are shown in table 6.

120 ml of the passivated supported ruthenium catalyst (1 wt % Ru on $ZrO_2$) were packed into a tubular reactor heated with an outer jacket (height: 1.4 m, interior diameter: 12 mm). Once initially flooded with hydrogen, the reactor was subsequently charged with a solution of 10 wt % of 4,4'-methylenedianiline (MDA). Hydrogenation was carried out at varying temperatures, with varying space velocities over the catalyst and also at a pressure of 140 bar, the reactor being operated with circulation, i.e., part of the discharge is recycled into the reactor. The reaction discharges were analyzed by gas chromatography and the isomer distribution was determined. The method is shown below. The results are shown in table 6 and show that the isomer ratio can be advantageously influenced by selection of the space velocity over the catalyst and the temperature.

TABLE 6

| No. | Reaction time [h] | Space velocity over the catalyst [kg/(kg*h)] | T [° C.] | Conversion [%] | PACM selectivity [%] | Isomer ratio | | |
|---|---|---|---|---|---|---|---|---|
| | | | | | | trans/trans | cis/trans | cis/cis |
| 3.1 | 1-149 | 0.04 | 140 | 95 | 95 | 51 | 40 | 9 |
| 3.2 | 364-477 | 0.04 | 80 | 67 | 60 | 19 | 49 | 33 |
| 3.3 | 1369-1377 | 0.02 | 77 | 78 | 73 | 20 | 49 | 31 |
| 3.4 | 1393-1424 | 0.02 | 60 | 47 | 32 | 18 | 48 | 34 |
| 3.5 | 1473-1539 | 0.02 | 90 | 85 | 86 | 22 | 49 | 29 |
| 3.6 | 1539-1561 | 0.04 | 90 | 72 | 74 | 21 | 49 | 30 |
| 3.7 | 1639 | 0.08 | 90 | 54 | 64 | 19 | 49 | 32 |

PACM denotes 4,4'-diaminodicyclohexylmethane

Analysis by Gas Chromatography:

| Column: | 30 m RTX5 amine; 0.25 mm; 0.5 µm |
|---|---|
| Temperature Program: | 80° C. - 0 min - 20° C./min - 200° C. - 0 min - 4° C./min - 260° C. - 5 min => 26 min total run time |
| Retention times [min]: | trans, trans 18.39 |
| | cis, trans 18.58 |
| | cis, cis 18.75 |
| | MDA (reactant) 25.00 |

The invention claimed is:

1. A process for hydrogenating at least one of 4,4'-methylenedianiline and polymeric methylenedianiline, the process comprising:
hydrogenating at least one of 4,4'-methylenedianiline and polymeric methylenedianiline with hydrogen in the presence of a catalyst,
wherein
the catalyst comprises ruthenium on a zirconium oxide support material, and
the zirconium oxide support material has a BET surface area of from 73 to 300 m²/g.

2. The process according to claim 1, which is carried out in suspension or in a fixed bed.

3. The process according to claim 2, wherein the zirconium oxide support material of the catalyst, present as a fixed bed catalyst, has a pore size distribution where more than 50% of the pores present are formed by mesopores having a diameter of from 2 nm to 50 nm and the remainder to 100% are formed by macropores having a diameter of >50 nm.

4. The process according to claim 2, wherein the catalyst, present as a fixed bed catalyst, has a pore size distribution where more than 50% of the pores present are formed by mesopores having a diameter of from 2 nm to 50 nm and the remainder to 100% are formed by macropores having a diameter of >50 nm.

5. The process according to claim 2, wherein the zirconium oxide support material of the catalyst, present as a suspension catalyst, has a pore size distribution where more than 40% of the pores present are macropores having a diameter of >50 nm and the remainder to 100% are formed by mesopores having a diameter of from 2 nm to 50 nm.

6. The process according to claim 2, wherein the catalyst, present as a suspension catalyst, has a pore size distribution where more than 40% of the pores present are formed by macropores having a diameter of >50 nm and the remainder to 100% are formed by mesopores having a diameter of from 2 nm to 50 nm.

7. The process according to claim 1, which is carried out as a continuous operation or batchwise.

8. The process according to claim 2, which is carried out in a fixed bed at a temperature of from 50 to 190° C.

9. The process according to claim 2, which is carried out in suspension at a temperature of from 50 to 190° C.

10. The process according to claim 1, which is carried out at a pressure of from 60 to 300 bar.

11. The process according to claim 1, wherein the catalyst comprises ruthenium in an amount of from 0.05 to 20 wt % based on the whole catalyst.

12. The process according to claim 1, wherein the zirconium oxide support material is present in at least one of a monoclinic phase, a tetragonal phase, a cubic phase and an amorphous phase.

13. The process according to claim 1, wherein the zirconium oxide support material is present in at least one of a monoclinic phase and a tetragonal phase.

14. The process according to claim 1, wherein the zirconium oxide support material has
a pore volume of from 0.1 to 1 cm³/g, and
a tamped density of from 500 to 2000 kg/m³.

15. The process according to claim 1, wherein the catalyst has
a BET surface area of from 78 to 300 m²/g,
a pore volume of from 0.1 to 1 cm³/g, and
a tamped density of from 500 to 2000 kg/m³.

16. The process according to claim 1, wherein the reaction time of said hydrogenating is from 10 to 400 min.

17. The process according to claim 1, wherein said hydrogenating is carried out in an organic solvent.

18. The process according to claim 1,
wherein a mixture is obtained from said hydrogenating and comprises
isomers of 4,4'-diaminodicyclohexylmethane when 4,4'-methylenedianiline is hydrogenated, and
oligomeric or polymeric ring-hydrogenated compounds when the polymeric methylenedianiline is hydrogenated;
wherein the isomers of 4,4'-diaminodicyclohexylmethane comprise trans, trans isomer of 4,4'-diaminodicyclohexylmethane in an amount of from 10 to 30 wt %, cis, trans isomer of 4,4'-diaminodicyclohexylmethane in an amount of from 30 to 55 wt %, and cis, cis isomer of 4,4'-diaminodicyclohexylmethane in an amount of from 10 to 50 wt %, based on a total amount of all isomers present; and
wherein the oligomeric or polymeric ring-hydrogenated compounds comprise trans, trans isomeric unit of 4,4'-diaminodicyclohexylmethane in an amount of from 10 to 30 wt %, cis, trans isomeric unit of 4,4'-diaminodicyclohexylmethane in an amount of from 30 to 55 wt %, and cis, cis isomeric unit of 4,4'-diaminodicyclohexylmethane in an amount of from 10 to 50 wt %, based on a total amount of all isomeric repeating units.

19. The process according to claim 1, wherein a mixture obtained from said hydrogenating
comprises isomers of 4,4'-diaminodicyclohexylmethane when 4,4'-methylenedianiline is hydrogenated and oligomeric or polymeric ring-hydrogenated compounds when the polymeric methylenedianiline is hydrogenated, and
has a melting point of less than 40° C.

20. A method of making a compound, the method comprising
reacting a mixture obtained by the process of claim 18 to obtain the compound, which is a surfactant, a medicament, a crop protection agent, a stabilizer, a polymer, a polyimide, an isocyanate, a hardener for an epoxy resin, a catalyst for polyurethane synthesis, an intermediate for preparing a quaternary ammonium compound, a plasticizer, a corrosion inhibitor, a synthetic resin, an ion exchanger, a textile auxiliary, a dye, a vulcanization accelerant, an emulsifier, or a starter for urea or polyurea synthesis.

* * * * *